United States Patent [19]

Shepherd et al.

[11] 4,058,550

[45] Nov. 15, 1977

[54] POLYSUBSTITUTED-ALKYL ESTERS OF 4-ALKYLAMINOBENZOIC ACIDS

[75] Inventors: Robert Gordon Shepherd, South Nyack; Thomas Gary Miner, Sugar Loaf, both of N.Y.

[73] Assignee: American Cyanamid Company, Stamford, Conn.

[21] Appl. No.: 625,989

[22] Filed: Oct. 28, 1975

[51] Int. Cl.$^2$ ............................................ C07C 101/00
[52] U.S. Cl. .................................. 560/43; 260/340.7; 260/340.9 R; 260/348.44; 424/310; 536/4; 536/115

[58] Field of Search ...................... 424/310; 260/471 R

[56] References Cited

U.S. PATENT DOCUMENTS

| | | | |
|---|---|---|---|
| 3,681,394 | 8/1972 | Sherlock | 424/310 X |
| 3,868,416 | 2/1975 | Albright et al. | 260/471 R X |
| 3,957,850 | 5/1976 | Bouchara | 260/471 R |

*Primary Examiner*—Ethel G. Love
*Attorney, Agent, or Firm*—Denis A. Polyn

[57] ABSTRACT

Polysubstituted-alkyl esters of 4-alkylaminobenzoic acids having hypolipemic activity.

9 Claims, No Drawings

POLYSUBSTITUTED-ALKYL ESTERS OF 4-ALKYLAMINOBENZOIC ACIDS

BACKGROUND OF THE INVENTION

The compounds of this invention are new and novel esters of the 4-alkylaminobenzoic acids described in U.S. Pat. No. 3,868,416 and have superior, biological and pharmacological properties. No hypolipemic activity has been reported in the literature for these compounds and they are different in structure and superior in action to other hypolipemic agents. The compounds of this invention lower serum-lipid concentrations and also decrease the deposition of lipids in the aorta. Esters such as these of glycerol and the like are designated to facilitate the intestinal absorptive process and to provide a reliable and high degree of absorption following the oral administration required of hypolipidemic agents. To the extent that these esters are hydrolyzed in the body they have the added advantage, relative to other esters, of producing a hydroxylated compound which is innocuous and is in fact a natural component of mammalian physiological processes. The novel esters of this invention are more completely and more uniformly absorbed from the gastrointestinal tract than the carboxylic acids and other esters. Also they cause less gastrointestinal irritation other than the corresponding carboxylic acids.

DESCRIPTION OF THE INVENTION

This invention relates to new organic compounds and more particularly it is concerned with novel polysubstituted-alkyl esters of 4-alkylaminobenzoic acids which may be presented by the following formula:

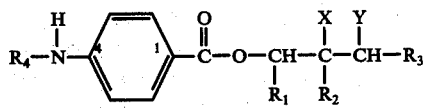

wherein $R_4$ is an unbranched or branched alkyl group $C_nH_{2n+1}$ wherein $n$ is 8 to 19; $R_1$, $R_2$ and $R_3$ are selected from the group consisting of hydrogen, $C_1$-$C_3$ alkyl, $C_1$-$C_3$ hydroxyalkylene, and $C_1$-$C_3$ hydroxyalkylenecarboxaldehyde in which case a tetrahydrofuran or pyran ring is formed when X is OH, and $R_2$ or $R_3$ combined with the appropriate X or Y may constitute a double-bonded oxygen atom; X and Y, which may be the same or different, are selected from the group consisting of hydrogen, hydroxy, loweralkanoyloxy, 4-alkylaminobenzoyloxy, hydroxymethyl, and, when taken together X and Y can comprise a carbon-carbon bond, a cyclic ether linkage (—O—), or a cyclic acetal or ketal (—O—CRR'—O— with R and R' being selected from the group consisting of hydrogen, loweralkyl and phenyl); where the alkylaminobenzoyloxy moiety and X may be interchanged; and the pharmaceutically acceptable salts thereof.

A preferred embodiment of this invention consists of those compounds wherein $R_4$ is an unbranched or branched alkyl group, $C_nH_{2n+1}$ wherein $n$ is 8 to 19; $R_1$ is hydrogen; $R_2$ and $R_3$ are both hydrogen, or one of them combined with the appropriate X or Y constitutes a double-bonded oxygen atom; X and Y, which may be the same or different, are selected from the group consisting of hydroxy or lower alkanoyloxy, and, when taken together X and Y can comprise a carbon-carbon bond, a cyclic ether linkage (—O—), or a cyclic acetal or ketal (—O—CRR'—O— with R and R' selected from the group consisting of hydrogen, $C_1$-$C_3$ alkyl and phenyl); wherein the 4-alkylaminobenzoyloxy moiety and X may be interchanged; and the pharmaceutically acceptable salts thereof.

The invention contemplates a method for lowering serum lipids and for decreasing aortic deposition of lipids in mammals by the administration of said esters.

The novel compounds of this invention are, in general, colorless crystalline solids having characteristic melting points and spectral properties. They are soluble in organic solvents such as chloroform, benzene, dichloromethane, acetonitrile, dimethylformamide, dimethylsulfoxide and lower alkanols. They are generally insoluble in water. These compounds are bases which form pharmaceutically acceptable salts with acids such as sulfuric, hydrochloric, phosphoric, succinic, citric and the like.

Suitable ester moieties contemplated by the present invention are glycerol, 2,3-epoxy-1-propanol (glycidol), 1,3- and 1,2-propanediol, $O_2$-acetylglycerol, $O_2$, $O_3$-diacetylglycerol, $O_3$-(4-alkylaminobenzoyl)glycerol, erythritol, 1,2,3,5-tetrahydroxypentane, pentaerythritol, ribose, glucose, glyceraldehyde, dihydroxyacetone, mannitol, sorbitol, 1,4-butanediol, 2,3-isopropylideneglycerol, 2,3-benzylideneglycerol, allyl alcohol, 1,4-butanediol and the like.

Suitable alkyl groups contemplated by the present invention are n-hexadecyl, n-pentadecyl, n-heptadecyl, 2-tridecyl and the like. The N-loweralkanoyl derivatives of I are active to the extent that they are deacylated in vivo to compounds of structure I.

These novel polysubstituted-alkyl 4-alkylaminobenzoates are prepared by reaction of sodium or other salts of the 4-alkylaminobenzoic acids with the appropriate polysubstituted-alkyl halides, sulfates, tosylates, trifluoromethyl sulfonates, or the like (II) in aqueous or anhydrous hexamethylphosphoramide, dimethylformamide, acetonitrile or other suitable solvents at 20°-160° C. The salts may be formed in situ from the 4-alkylaminobenzoic acids and the appropriate bases.

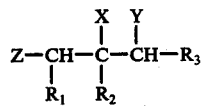

where Z = the leaving groups mentioned above

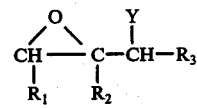

A similar and chemically related method of preparation is the reaction of the 4-alkylaminobenzoic acids or certain of their salts with substituted-alkylene oxides (III) at 20°-160° C.

The polysubstituted-alkyl 4-alkylaminobenzoates of the present invention are also synthesized by reaction of the polysubstituted-alkyl alcohols (IV)

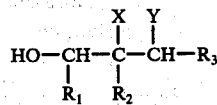

with the 4-alkylaminobenzoyl chloride hydrochlorides in the presence of bases, or alternatively, with the 4- alkylaminobenzoic acids using acid catalysis with toluenesulfonic acid and the like or with Lewis acid catalysts. The polysubstituted-alkyl esters are also prepared by transesterification of methyl or ethyl 4-alkylaminobenzoates with polysubstituted-alkyl alcohols (IV) using acidic or basic catalysis.

Certain syntheses of these polysubstituted-alkyl 4-alkylaminobenzoates may also involve the formation of the desired X and Y groups as the final step in the process. For example, when X and/or Y are alkanoyloxy or 4-alkylaminobenzyloxy in the desired structure (I), these moieties are produced by acylation of the corresponding compounds in which X and/or Y are hydroxy groups or taken together represent an epoxy group. Similarly, when X and Y taken together form a cyclic acetal or ketal moiety in the desired structure (I), such a moiety is produced by acid-catalyzed reaction of structure (I) (where X and Y are both hydroxy) with an aldehyde or ketone. The reverse reaction in certain cases is also used to form the dihydroxy compounds of structure (I) from acetal or ketal derivatives. When X and/or Y are halogen groups in structure (I) the corresponding hydroxy compounds are obtained by treatment with silver nitrite followed by mild hydrolysis. Dihydroxy compounds of structure (I) are also obtained by gentle acid-catalyzed hydrolytic opening of the epoxide ring in epoxyalkyl 4-alkylaminobenzoates. Similar dihydroxy compounds of structure (I) result from dihydroxylation of alkenyl 4-alkylaminobenzoates.

The novel 4-alkylaminobenzoate esters of the present invention are prepared by reaction of polysubstituted-alkyl 4-aminobenzoates with suitable alkylating agents such as alkyl halides, sulfates, tosylates, or trifluoromethylsulfonates with or without solvent at 50° to 150° C. Suitable solvents are lower alkanols, chloroform, N,N-dimethylformamide, N,N-dimethylacetamide hexamethylphosphoramide, diglyme, dimethyl sulfoxide, acetonitrile, toluene benzene and the like. The reaction may be carried out with an equivalent of the 4-aminobenzoate ester in excess, using it as the base, or with an equivalent of another base such as an alkali carbonate or bicarbonate, or with a catalytic amount of copper powder when alkali halides are used as the alkylating agent. Alternatively, the desired 4-alkylaminobenzoate esters are prepared by reaction of the corresponding 4-aminobenzoate ester with an alkyl halide of 8 to 19 carbon atoms in the presence of an equivalent of sodium hydride in an inert solvent such as N,N-dimethylformamide, N,N-dimethylacetamide and diglyme at 50°-150° C. The introduction of the N-alkyl group in structure (I) is also accomplished by catalytic reductive alkylation of polysubstituted-alkyl esters of 4-aminobenzoic acid or of 4-nitrobenzoic acid with the appropriate aliphatic aldehyde or ketone. It may also be introduced by copper chromite-catalyzed reduction of polysubstituted-alkyl 4-alkanoylaminobenzoates.

We have now found that certain members of this class can safely and effectively lower serum sterols, and triglycerides in warm-blooded animals. These hypolipidemic properties would be expected to be useful in the treatment of atherosclerosis. Atherosclerosis is a form of arteriosclerosis where chloresterol and lipoid materials are deposited as plaques in the intima of large and medium-sized arteries. Arteriosclerosis is associated with the degeneration of arterial walls by mechanisms not clearly defined. However, there is a statistical correlation between hypercholesteremia and the incidence of cardiovascular disease, particularly ischemic heart disease. For some time it has been considered desirable to lower high cholesterol, triglyceride, and phospholipid levels in mammals as a possible preventive measure against atherosclerosis. In the past, attempts have been made to lower the levels of cholesterol in the blood by the oral feeding of various substance which have been generally referred to in the art as hypocholesteremic adjuvants. Typical of such substances are lecithin, cottonseed oil and corn oil. In addition, three synthetic lipid-lowering agents are availble, namely, clofibrate, D-thyroxine, and nicotinic acid [R. I. Levy and D. S. Frederickson, Postgraduate Medicine Vol. 47, pages 130–126 (1970)]. The compounds of the present invention exert a more powerful hypocholesteremic action than the aforementioned adjuvants and synthetic drugs. In addition, these compounds have the ability to arrest safely and effectively the development of atheromatous lesions in the aorta of warm-blooded animals, thereby possessing an important additional way of combating atherosclerosis. It is not known how the novel compounds or method of treatment of the present invention operate in blood serum and no theory of why these compounds so operate is advanced. It is not intended that the present invention should be limited to any particular mechanism of their action.

The compounds of the present invention are hypolipidemic agents and were shown to possess hypolipidemic activity as determined by animal experiments as follows: the compounds studied were administered orally admixed with the diet to groups of 4 male rats, CFE strain from Carworth Farms. A control group of 8 rats was mantained on the diet alone; test groups were maintained on the diet plus the indicated percentage of compound by weight. After 6 days or 4 weeks the animals were sacrificed and serum-sterol concentrations in milligrams per 100 milliliters were determined either (1) according to the saponification and extraction method of P. Trinder, Analyst 77, 321 (1952) and the colorimetric determination of Zlatkis, et al., J. Lab. Clin. Med. 44, 486 (1953) or (2) by the extraction method of H. H. Leffler, Amer. J. Clin. Path. 31, 310 (1959), and the colorimetric determination of Zlatkis (vide supra), the overall method appropriately modified for use with an automatic mechanical analyzer. Sermum triglycerides were estimated by the automated procedure of Kessler and Lederer ("Automation in Analytical Chemistry" Skeggs, L. T. (Ed.), Mediad Inc., New York, 1965, p. 341).

In these tests, a compound is considered to have hypolipidemic activity if it depresses the serum-sterol concentration below that of the controls, and/or depresses triglyceride concentration below that of the controls. Table I shows several of the compounds of the present invention and the degree to which they depress serum sterols and triglycerides after a 6-day dosing period and after a 4-week dosing period.

TABLE I

Hypolipidemic Activity of Polysubstituted-alkyl 4-Alkylaminobenzoates in Rats

| Compound | % Compound in Diet | 1-Week Test, % Lowering of Serum | | 4-Week Test, % Lowering of Serum | |
|---|---|---|---|---|---|
| | | Sterol | Triglyceride | Sterol | Triglyceride |
| 2,3-Dihydroxypropyl-4-(n-hexadecylamino)benzoate | 0.10 | 42 | 57 | | |
| | 0.071 | 28 | 62 | 31 | 57 |
| | 0.03 | 29 | 45 | 28 | 45 |
| | 0.01 | 21 | 24 | 23 | 23 |
| | 0.003 | 1 | 19 | | |
| 2,3-Epoxypropyl-4-(n-hexadecylamino)benzoate | 0.1 | 25 | 47 | | |
| | 0.03 | 25 | 40 | | |
| | 0.01 | 8 | 26 | | |
| 2,3-Dihydroxypropyl 4-(n-hexadecylamino)benzoate hydrochloride | 0.1 | 31 | 68 | | |
| 2-Acetoxy-3-hydroxypropyl 4-(n-hexadecylamino)benzoate | 0.1 | 15 | 52 | | |
| | 0.03 | 15 | 29 | | |
| 2,3-(Isopropylidenedioxy)-propyl 4-(n-hexadecylamino)benzoate | 0.1 | 5 | 32 | | |
| 2-Phenyl-1,3-dioxolan-4-ylmethyl 4-(n-hexadecylamino)benzoate | 0.1 | 17 | 50 | | |
| 2-hydroxypropyl 4-(n-hexadecylamino)benzoate | 0.1 | 17 | 53 | | |
| | 0.03 | 23 | 33 | | |
| | 0.01 | 12 | 26 | | |
| 2-Propenyl 4-(n-hexadecylamino)benzoate | 0.1 | 19 | 40 | | |
| | 0.03 | none | 40 | | |
| 3-Hydroxypropyl 4-(n-hexadecylamino)benzoate | 0.1 | 42 | 62 | | |
| | 0.03 | 26 | 19 | | |
| | 0.01 | 23 | 28 | | |

For the mouse study, CFE mice from the Roscoe B. Jackson Memorial Laboratories, Bar Harbor, Main were used. The methods used for lipid analysis were the same as those used for the rat study. The results obtained on using 2,3-dihydroxypropyl 4-(n-hexadecylamino)benzoate are shown in Table II.

Table II

Hypolipidemic Activity of Polysubstituted-alkyl 4-Alkylaminobenzoates in Mice

| Compound | % Compound in Diet | 1-Week Test, % Lowering of Serum | |
|---|---|---|---|
| | | Sterol | Triglyceride |
| 2,3-Dihydroxypropyl 4(n-hexadecylamino)benzoate | 0.1 | 18 | 19 |
| | 0.03 | 11 | 30 |
| | 0.01 | 9 | 6 |

Compounds of this invention demonstrated the ability to arrest the development of atheromatous lesions using rabbits as an animal model. Thus they combat atherosclerosis by means of this ability as well as by means of their ability to lower serum-lipid concentrations. The atheromatous lesions were induced by mild mechanical injury of the surface of the aorta of rabbits. After feeding a cholesterol-supplemented diet followed by diet containing these componds, histological and biochemical analyses of the aortic tissue and masurement of the extent and severity of the lesions were carried out. The results with 2,3-dihydroxypropyl 4-(n-hexadecylamino)benzoate illustrate the beneficial effect of these compounds. The amount of sterol deposited in the aorta of treated rabbits was reduced by 40% in the thoracic segment and by 36% in the abdominal segment of the aorta compared to the untreated controls. The extent of formation of atheromatous lesions, measured by the percentage of the aorta having such lesions, was reduced by 95% in the thoracic segment and by 75% in the abdominal segment, compared to the untreated controls.

By using the monkey as an animal model and radiolabeling for analytical purposes, the 2,3-dihydroxypropyl 4-(n-hexadecylamino)benzoate was shown to be much better absorbed than the corresponding acid of U.S. Pat. No. 3,868,416 after the oral dosing requiring of a hypolipidemic agent. The ability to lower serum lipids and to decrease deposition of lipids on the aortic walls is directly increased in proportion to the degree of absorption from the intestine. The concentration of radiolabeled drug in the bloodstream was found to be 4 times as high with 2,3-dihydroxypropyl 3-(n-hexadecylamino)benzoate as with the corresponding acid.

The clinically used dose of clofibrate is 2 g/day and its effective dose in rats is 0.3% of diet. The compounds of this invention show a comparable effect on serum lipids in rats at doses of only 0.1% to 0.01%. Therefore, the range of doses should be between about 50 mg to 1 g/day in single or divided doses using a 50 kg human as a model. The effective range of the compounds described in this invention would be between about 0.5 and 40 mg/kg/day.

The lipid-lowering agents of the present invention may be orally administered, for example, with an inert diluent or with an assimilable edible carrier, or they may be enclosed in hard of soft gelatin capsules, or they may be compressed into tables, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contain between about 10 and 500 miligrams of active compound.

The tablets, troches, pills, capsules and the like may also contain the following: a binder such as gum tragacanth, acacia, corn starch or gelatin; an excipient such as dicalcium phosphate; a disintegrating agent such as corn starch, pototo starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar, or both. A syrup or elixir may contain the activity compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

In addition, the active ingredients may be incorporated into sustained release preparations. Preparations of this type would contain greater quantities of the active ingredients.

EXAMPLE 1

2,3-Dihydroxypropyl 4-(n-hexadacylamino)benzoate

A solution of 7.34 g of 4-(n-hexadecylamino)benzoic acid, 4.80 g of 25% aqueous sodium hydroxide, and 12.6 g of 3-iodo-1,2-propanediol in 50 ml of hexamethylphosphoramide is stirred for 24 hours at ambient temperature, diluted with 100 ml of ether and stirred for 5 days at ambient temperature. The mixture is treated with water and extracted with ether. The dried extracts are evaporated to yield 2,3-dihydroxypropyl 4-(n-hexadecylamino)benzoate, m.p. 112° C.

EXAMPLE 2

2,3-Dihydroxypropyl 4-(n-hexadecylamino)benzoate

A solution of 7.20 g of 4-(n-hexadecylamino)benzoic acid in 25 ml of hexamethylphosphoramide is added to a stirred mixture of 0.800 g of sodium hydride (57% in mineral oil) and 25 ml of hexamethylphosphoramide. The soluion which forms after one hour is treated with 11.0 g of 1-chloro-2,3-propanediol and is then stirred at 60° C for 18 hours. Dilution with water followed by filtration affords a white solid which is crystallized from ethanol to yield 2,3-dihydroxypropyl 4-(n-hexadecylamino)benzoate melting at 112°-113° C.

EXAMPLE 3

2,3-Dihydroxypropyl 4-(n-hexadecylamino)benzoate

A solution of 7.35 g of 4-(n-hexadecylamino)benzoic acid in 50 ml of hexamethylphosphoramide is treated with 4.80 g of 25% aqueous sodium hydroxide followed by 11.0 g of 3-chloro-1,2-propanediol and then is heated at 140° C for 6 hours. The mixture is diluted with water and ether and filtered to yield a white solid. Recrystallization from acetonitrile and then from carbon tetrachloride affords analytically pure 2,3-dihydroxypropyl 4-(n-hexadecylamino)benzoate, mp 112°-113° C.

EXAMPLE 4

2,3-Dihydroxypropyl 4-(n-hexadecylamino)benzoate

A solution of 57.5 g of sodium 4-(n-hexadecylamino)benzoate and 55.0 g of 3-chloro-1,2-propanediol in 350 ml of hexamethylphosphoramide is treated in the manner described in Example 3 to yield 2,3-dihydroxypropyl 4-(n-hexadecylamino)benzoate melting at 112°-113° C.

EXAMPLE 5

2,3-Dihydroxypropyl 4-(n-hexadecylamino)benzoate

A mixture of 100 mg of 2,3-epoxypropyl 4-(n-hexadecylamino)benzoate, 0.2 ml of 1N sulfuric acid, and 1.0 ml of 1,2-dimethoxyethane is heated under reflux for one hour, diluted with water, and filtered to yield 2,3-dihydroxypropyl 4-(n-hexadecylamino)benzoate as a white solid, mp 112°C.

EXAMPLE 6

2,3-Dihydroxypropyl 4-(n-hexadecylamino)benzoate

A mixture of 2.25 g of methyl 4-(n-hexadecylamino)benzoate, 280 mg of glycerol, and 1.37 g of p-toluenesulfonic acid is heated at 180° C for 18 hours and then is partitioned between ether and 3% aqueous carbonate solution. The ether layer is separated, dried, and evaporated to yield 2,3-dihydroxypropyl 4-(n-hexadecylamino)benzoate.

EXAMPLE 7

2,3-Dihydroxypropyl 4-(n-hexadecylamino)benzoate

A mixture of 722 mg of 4-(n-hexadecylamino)benzoic acid, 736 mg of glycerol, and 412 mg of p-toluene sulfonic acid is heated for 4 hours at 120° C, allowed to cool, and then is treated with ether and 2% aqueous sodium carbonate solution. Filtration affords a white solid which is recrystallized from chloroform to yield 2,3-dihydroxypropyl 4-(n-hexadecylamino)benzoate, mp 112° C.

EXAMPLE 8

2,3-Dihydroxypropyl 4-(n-hexadecylamino)benzoate

A solution of 11.8 g of 4-(n-hexadecylamino)benzoic acid, 1.00 g of glycerol, and 5.35 ml of boron trifluoride etherate in 200 ml of toluene is stirred under reflux for 48 hours. The solution is treated with an additional 5.35 ml of boron trifluoride etherate and refluxing is continued for 120 hours. Dilution with water and methylene chloride followed by filtration affords 2,3-dihydroxypropyl 4-(n-hexadecylamino)benzoate as a white solid.

EXAMPLE 9

2,3-Dihydroxypropyl 4-(n-hexadecylamino)benzoate hydrochloride

A solution of 15.0 g of 2,3-dihydroxypropyl 4-(n-hexadecylamino)benzoate in 700 ml of carbon tetrachloride is stirred under reflux and is treated with anhydrous hydrogen chloride. The mixture is allowed to cool and is filtered to yield 2,3-dihydroxypropyl 4-(n-hexadecylamino)benzoate hydrochloride as a white solid, mp 126°-130° C.

EXAMPLE 10

Methyl 4-(n-hexadecylamino)benzoate

A solution of 50.5 g of 4-(n-hexadecylamino)benzoic acid and 34.4 ml of boron trifluoride etherate in 200 ml of methanol is stirred under reflux for 44 hours, allowed to cool, and is poured into 1.20 liters of ice cold 5% aqueous sodium carbonate solution. The white solid is collected by filtration and recrystallized from benzene-ethanol to yield methyl 4-(n-hexadacylamino)benzoate, mp 92°–93° C.

EXAMPLE 11

2,3-Epoxypropyl 4-(n-hexadecylamino)benzoate

A mixture of 89.0 g of epichlorohydrin, 92.0 g of sodium 4-(n-hexadecylamino)benzoate, and 350 ml of hexamethylphosphoramide is stirred at 105° C for 5 hours, allowed to cool, and poured into 1.0 liter of water. The white solid is collected by filtration, recrystallized from acetonitrile and then from hexane-methylene chloride to yield 2,3-epoxypropyl 4-(n-hexadecylamino)benzoate, mp 86°–89° C.

EXAMPLE 12

2,3-(Isopropylidenedioxy)propyl 4-(n-hexadecylamino)benzoate

A mixture of 8.70 g of 2,3-dihydroxypropyl 4-(n-hexadecylamino)benzoate, 1.10 g of anhydrous hydrogen chloride, 3.90 g of sodium sulfate, and 550 ml of acetone is stirred under reflux for 2 hours and then filtered while hot. The filtrate is cooled and the precipitate collected by filtration. A mixture of the solid, 200 ml of chloroform, 8.0 ml of methanol, and 14 g of sodium carbonate is stirred for 18 hours and filtered. The filtrate is evaporated and the residual white solid recrystallized from isopropyl alcohol to yield 2,3-(isopropylidenedioxy)propyl 4-(n-hexadecylamino)benzoate, mp 87°–88° C.

EXAMPLE 13

2-Acetoxy-3-hydroxypropyl 4-(n-hexadecylamino)benzoate

A mixture of 8.35 g of 2,3-epoxypropyl 4-(n-hexadecylamino)benzoate and 7.0 ml of acetic acid is heated at 100° C for four hours, allowed to cool, and diluted with water. Filtration affords 2-acetoxy-3-hydroxypropyl 4-(n-hexadecylamino)benzoate, mp 67° C unchanged by recrystallization.

EXAMPLE 14

2,3-Diacetoxypropyl N-acetyl-4-(n-hexadecylamino)benzoate

A solution of 6.53 g of 2,3-dihydroxypropyl 4-(n-hexadecylamino)benzoate in 100 ml of chloroform is stirred under reflux while 9.0 ml of acetic anhydride is added and for 6 hours thereafter. The solution is extracted with 2% aqueous sodium carbonate solution and water, dried, and evaporated to yield 2,3-diacetoxypropyl N-acetyl-4-(n-hexadecylamino)benzoate as a yellow oil.

EXAMPLE 15

4-(n-Hexadecylamino)benzoic acid hydrochloride

A solution of 2.00 g of 4-(n-hexadecylamino)benzoic acid in 80 ml of methylene chloride is stirred at 35° C and treated with anhydrous hydrogen chloride. The resulting mixture is chilled and filtered to yield 4-(n-hexadecylamino)benzoic acid hydrochloride as a white solid.

EXAMPLE 16

4-(n-Hexadecylamino)benzoyl chloride hydrochloride

A mixture of 1.00 g of 4-(n-hexadecylamino)benzoic acid hydrochloride and 5.00 ml of thionyl chloride is allowed to stand at ambient temperature for 20 hours and then is concentrated in vacuo to yield 4-(n-hexadecylamino)benzoyl chloride hydrochloride as an orange solid.

EXAMPLE 17

2-Phenyl-1,3-dioxan-5-yl 4-(n-hexadecylamino)benzoate

A solution of 450 mg of 1,3-benzylideneglycerol and 1.22 g. of 4-dimethylaminopyridine in 10 ml. of methylene chloride is treated with 1.16 g. of 4-(n-hexadecylamino)benzoyl chloride hydrochloride and after 15 minutes the solution is washed with water, dried over anhydrous magnesium sulfate, and evaporated. The 2-phenyl-1,3-dioxan-5-yl 4-(n-hexadecylamino)benzoate, mp 115°–117° C., is separated from the residue by chromatography using silica gel as the adsorbant.

EXAMPLE 18

1,3-Dihydroxy-2-propyl 4-(n-hexadecylamino)benzoate

A mixture of 2-phenyl-1,3-dioxan-5-yl 4-(n-hexadecylamino)benzoate, palladium black, and acetic acid is shaken under one atmosphere of hydrogen until hydrogen uptake ceases. The catalyst is separated by filtration and the solvent is evaporated. Crystallization from acetonitrile affords 1,3-dihydroxy-2-propyl 4-(n-hexadecylamino)benzoate as a white solid.

EXAMPLE 19

4-Hydroxybutyl 4-(n-hexadecylamino)benzoate

A mixture of 7.66 g of sodium 4-(n-hexadecylamino)benzoate, 7.55 g of 4-chloro-1-butanol, and 20.0 ml of hexamethylphosphoramide is stirred at 150° C for two hours, allowed to cool, and poured into water. The solid is collected by filtration and then is dissolved in methylene chloride. The solution is washed with water, dried, and evaporated. The residual solid is crystallized from hexane to yield 4-hydroxybutyl 4-(n-hexadecylamino)benzoate as a white solid, mp 61°–63° C.

EXAMPLE 20

3-Hydroxypropyl 4-(n-hexadecylamino)benzoate

In the manner described in Example 19, treatment of 3-bromopropanol with sodium 4-(n-hexadecylamino)benzoate affords 3-hydroxypropyl 4-(n-hexadecylamino)benzoate, mp 67°–69° C.

EXAMPLE 21

1,2,3-Tris(4-n-hexadecylaminobenzoyloxy)propane

A mixture of 3.25 g. of 4-(n-hexadecylamino)benzoic acid, 0.276 g. of glycerine, and 2.17 g. of p-toluenesulfonic acid is heated to 140° C. overnight and then diluted with 20 ml. of 10% sodium carbonate solution and 20 ml. of chloroform. Separation of the organic layer and concentration yields a solid which is chromatographed on silica gel, which in turn yields a white solid. Crystallization from a mixture of methylene chloride and hexane yields 1,2,3-tris(4-n-hexadecylaminobenzoyloxy)propane as a solid, m.p. 117°–118° C.

EXAMPLE 22

1,2-Bis(4-n-hexadecylaminobenzoyloxy)propan-3-ol and
1,3-bis-(4-n-hexadecylaminobenzoyloxy)propan-2-ol A mixture of 4.34 g. of 4-(n-hexadecylamino)benzoic acid and 4.17 g. of 2,3-epoxypropyl-4-(n-hexadecylamino)benzoate is melted, under nitrogen, at 95°–100° C. and then heated at 115° C. for 24 hours. The solution is then cooled, diluted with 50 cc. of chloroform, and chromatographed on alumina with chloroform and ethanol. The white solid from the evaporation of the eluates is recrystallized from acetonitrile and then from carbon tetrachloride. The 1,2- and 1,3-bis(4-n-hexadecylaminobenzoyloxy)isomers are separated by preparative thin-layer chromatography, m.p. 101°–103°0 C.

EXAMPLE 23

2-Hydroxypropyl 4-(n-hexadecylamino)benzoate

A solution of 7.2 g. of 4-n-hexadecylaminobenzoic acid, 15.2 g. of 1,2-dihydroxypropane, and 3.9 ml. of boron trifluoride etherate are stirred together, under nitrogen, at 115° C. for 19 hours. The solution is cooled, diluted with methylene chloride, and placed in a freezer overnight. The solid is collected, washed with hexane, and oven-dried to yield a white solid. The solid is recrystallized from hexane and chromatographed on alumina with chloroform. This process yields 2-hydroxypropyl 4-(n-hexadecylamino)benzoate as a white solid, m.p. 91°–93° C.

The same product is obtained when 5.16 g of p-toluene sulfonic acid is used as catalyst instead of the boron trifluoride etherate.

EXAMPLE 24

2,3-Dihydroxypropyl 4-(N-acetyl-n-hexadecylamino)benzoate

A solution of 3.26 g. of 2,3-dihydroxypropyl-4-(n-hexadecylamino)benzoate and 0.85 ml. of acetic anhydride in 50 ml. of chloroform is heated to reflux for 1 hour and then cooled. The mixture is washed with 90 ml. of water and solid at the interface filtered. The chloroform layer on concentration in vacuo gives a residue which on trituration with methylene chloride yields a white solid (starting material) after filtration. The filtrate on concentration in vacuo yields a pale yellow oil. The oil is stirred overnight with water, extracted with chloroform and azeotroped free of acetic acid with benzene. The pale yellow oil obtained by evaporation in high vacuum is then chromatographed to remove a trace of N,O-diacetylated material. The liquid product is characterized by elemental analyses, infrared spectrum and nuclear magnetic resonance.

EXAMPLE 25

2,3-Diacetoxypropyl 4-(N-acetyl-n-hexadecylamino)benzoate and 3-Acetoxy-2-hydroxypropyl 4-(N-acetyl-n-hexadecylamino)benzoate A solution of 6.525 g. of 2,3-dihydroxypropyl-4-(n-hexadecylamino)benzoate and 21 ml. of acetic anhydride in 100 ml. of chloroform is heated to reflux for 3½ hours, cooled to room temperature and concentrated in vacuo to yield a pale yellow liquid. After adding 50 ml. of water and 50 ml. of chloroform to the liquid, the chloroform layer is separated and washed with water, dried over magnesium sulfate and filtered. Concentration of the filtrate in vacuo yields a pale yellow liquid. The liquid is chromatographed on silica gel using a 1:2 hexane-ethyl acetate mixture as the eluting solvent. The first fraction is shown by elemental analysis, infrared spectrum and nuclear magnetic resonance to be 2,3-diacetoxypropyl 4-(N-acetyl-n-hexadecylamino)benzoate. The second fraction is similarly shown to be 3-acetoxy-2-hydroxypropyl 4-(N-acetyl-n-hexadecylamino)benzoate.

EXAMPLE 26

2,3-Dihydroxypropyl 4-(n-hexadecylamino)benzoate

A solution of 3.8 g. sodium 4-(n-hexadecylamino)benzoate, 3.7 g. of epichlorohydrin, and 0.7 ml. of water in hexamethylphosphoramide is heated to 90° C. for 5 hours. An additional 0.7 ml. of water is added, followed by 1 ml. of 1N sulfuric acid. The reaction mixture is cooled after 1½ hours. After adding dimethoxyethane and benzene, the organic layer is separated and washed with water. The solvent is removed in vacuo to give a white solid which is recrystallized from 15 ml. of acetonitrile to yield 2,3-dihydroxypropyl 4-(n-hexadecylamino)benzoate. If this material contains any of the intermediate 2,3-epoxypropyl 4-(n-hexadecylamino)benzoate, it is removed by chromatography on silica gel.

EXAMPLE 27

2,3-Dihydroxypropyl 4-(n-hexadecylamino)benzoate

A solution of 3.6 g. of 4-(n-hexadecylamino)benzoic acid and 1.0 g. of 2,3-epoxypropan-1-ol in 100 ml. of hexamethylphosphoramide is heated at 90° C. for 8 hours. After addition of ether and water, the ether layer is separated and the ether extraction repeated several times. Following evaporation of the ether extracts, the mixture of starting material and desired, 2,3-dihydroxypropyl ester is separated by chromatography on silica gel and recrystallization from acetonitrile.

EXAMPLE 28

[2,2-Di-(hydroxymethyl)-3-hydroxy]propyl 4-(n-hexadecylamino)benzoate

A mixture of 3.62 g. of 4-(n-hexyldecylamino)benzoic acid, 5.44 g. of pentaerythritol, 7.60 g. of p-toluene sulfonic acid, and 100 ml. of toluene is stirred under reflux for 3 days and the water which is formed is collected in Dean-Stark trap. The mixture is extracted with aqueous sodium carbonate and the organic layer is separated, dried over anhydrous mangesium sulfate, and evaporated. Crystallization from chloroform affords (2,2-dihydroxymethyl-3-hydroxy)propyl 4-(n-hexadecylamino)benzoate.

EXAMPLE 29

(2,3-Dihydroxy-1-hydroxymethyl)propyl 4-(n-hexadecylamino)benzoate

A mixture of 3.62 g. of 4-(-n-hexadecylamino)benzoic acid, 4.88 g. of meso-erythritol, 7.60 g. of p-toluene sulfonic acid, and 100 ml. of toluene is stirred under reflux for 3 days and the water formed is collected in a Dean-Stark trap. The mixture is partitioned between aqueous sodium carbonate solution and dimethoxyethane. The organic layer is separated, dried over anhyrous magnesium sulfate, and evaporated. Crystallization from chloroform affords (2,3-dihydroxy-1-hydroxymethyl)propyl 4-(n-hexadecylamino)benzoate as a white solid, m.p. 123°–125° C.

EXAMPLE 30

2,3,4,5,6-Pentahydroxyhexyl 4-(n-hexadecylamino)benzoate

In the manner described in Example 7, 3.62 g. of 4-(n-hexadecylamino)benzoic acid, 1.82 g. of mannitol, and 2.06 g. of p-toluene sulfonic acid are reacted to yield a mixture of mono- and bis-acylated products. Pure 2,3,4,5,6-pentahydroxyhexyl 4-(n-hexadecylamino)benzoate is separated from the mixture by adsorption chromatography using silica gel as the adsorbant.

EXAMPLE 31

2,3-Dihydroxypropyl 4-(n-nonadecylamino)benzoate

A solution of 8.05 g. of 4-(n-nonadecylamino)benzoic acid in 25 ml. of hexamethylphosphoramide is treated with sodium hydride and then 1-chloro-2,3-propanediol in the manner described in Example 2 to yield 2,3-dihydroxypropyl 4-(n-nonadecylamino)benzoate as a white solid.

EXAMPLE 32

2,3-Dihydroxypropyl 4-(n-octylamino)benzoate

A solution of 4-(n-octylamino)benzoic acid (4.97 g.) in 25 ml. of hexamethylphosphoramide is treated with sodium hydride and then 1-chloro-2,3-propanediol in the manner described in Example 2 to produce white crystals of 2,3-dihydroxypropyl 4-(n-octylamino)benzoate.

EXAMPLE 33

2,3-Dihydroxypropyl 4-(n-tridecylamino)benzoate

A solution of 6.36 g. of 4-(n-tridecylamino)benzoic acid in 25 ml. of hexamethylphosphoramide is treated with sodium hydride and the 1-chloro-2,3-propanediol in the manner described in Example 2 to yield 2,3-dihydroxypropyl 4-(n-tridecylamino)benzoate as a white solid.

EXAMPLE 34

2-Phenyl-1,3-dioxolan-4-ylmethyl-4-(n-hexadecylamino)benzoate

A solution of 8.7 g. of 2,3-dihydroxypropyl 4-(n-hexadecylamino)benzoate and 21.2 g. of benzaldehyde in 100 ml. of toluene containing 1.1 g. of gaseous hydrochloric acid is heated to reflux for 3.5 hours cooled to room temperature. After concentration in vacuo to about 20 ml. and dilution with 50 ml. of hexane, the mixture is chilled in an ice-ethanol bath and filtered. The resulting solid is chromatographed on silica gel and then recrystallized from dichloromethane-hexane to yield the title compound, m.p. 74.5°–76.5° C.

EXAMPLE 35

2-Propenyl 4-(n-hexadecylamino)benzoate

A solution of 7.66 g. of sodium 4-(n-hexadecylamino)benzoate and 12.1 g. of allyl bromide in 100 ml. of dry hexamethylphosphoramide is added to a reaction flask. After 6 hours the solution is poured into 100 ml. of water and the solid collected and recrystallized from 50 ml. of acetonitrile. This material is recrystallized from hexanol to yield the title compound, m.p. 81°–83° C.

EXAMPLE 36

2,3-Diacetoxypropyl 4-(n-hexadecylamino)benzoate

To 4.21 g. of sodium hydride (washed free of mineral oil) is added a solution of 21.7 g. of 2,3-dihydroxypropyl 4-(n-hexadecylamino)benzoate in 150 ml. of hexamethylphosphoramide. After the evolution of hydrogen ceases, 9.4 ml. of acetic anhydride is added. After stirring 18 hours, the reaction mixture is treated with water and the product extracted into ethyl acetate. After chromatography, the product is recrystallized from methylene chloride-hexane mixture and melted at 68° C.

EXAMPLE 37

6-[4-(n-hexadecylamino)benzoyl]glucopyranose

A solution of 2.70 g. of 1,2,5,6-bisisopropylidene glucofuranose and 2.84 g. of 4-dimethylaminopyridine in 100 ; ml. of chloroform is treated with 4.16 g. of 4-(n-hexadecylamino)benzoyl chloride hydrochloride. After 16 hours at room temperature, the mixture is washed with water, dried over magnesium sulfate and evaporated. The residue of 3-[4-(n-hexadecylamino)benzoyl]-1,2,5,6-bisisopropylidene glucofuranose is dissolved in 80% trifluoroacetic acid at room temperature and the completion of the ketal cleavage followed by thin-layer chromatography. The solution is then vacuum evaporated at low temperature and the residual solid washed with sodium bicarbonate solution. After recrystallization from acetonitrile, the 6-[4-(n-hexadecylamino)benzoyl]glucopyranose is obtained as a white solid.

EXAMPLE 38

4-Hydroxy-2-buten-1-yl 4-(n-hexadecylamino)benzoate

To a mixture of 8.8 g. of 1,4-dihydroxy-2-butene and 2.84 g. of 4-dimethylaminopyridine is added 4.16 g. of 4-(n-hexadecylamino)benzoyl chloride hydrochloride. The heat evolution is moderated with ice and stirring is continued for 4 hours. Chloroform and water are added and the chloroform extract chromatographed to remove any diacylated by-product. Evaporation to crystallization yields the 4-hydroxy-2-buten-1-yl 4-(n-hexadecylamino)benzoate as a white solid.

EXAMPLE 39

3-Hydroxyacetonyl 4-(n-hexadecylamino)benzoate

The compound 4-(n-hexadecylamino)benzoyl chloride hydrochloride (4.16 g.) is added to a mixture of 3.6 g. of dihydroxyacetone and 2.44 g. of 4-dimethylaminopyridine in an ice bath. After 4 hours at room temperature, the mixture is treated with chloroform and water. The chloroform extract is chromatographed rapidly and evaporated in vacuo to yield 3-hydroxyacetonyl 4-(n-hexadecylamino)benzoate.

EXAMPLE 40

4-(n-Hexadecylamino)benzoyl glyceraldehyde

To a mixture of 3.6 g. of glyceraldehyde and 2.44 g. of 4-dimethylaminopyridine in an ice-bath is added 4.16 g. of 4-(n-hexadecylamino)benzoyl chloride hydrochloride. After 4 hours at room temperature, chloroform and water are added. The chloroform extract is chromatographed quickly and evaporated in vacuo to yield 4-(n-hexadecylamino)benzoyl glyceraldehyde.

EXAMPLE 41

4-Hydroxy-3-hydroxymethyl-2-pentyl 4-(n-hexadecylamino)benzoate

A 13.4 g. of 2,4-dihydroxy-3-hydroxymethylpentane solution in dimethoxyethane is added to 2.4 g. of sodium hydride (washed free of mineral oil). After hydrogen evolution ceased, 12.65 g. of benzyl chloride is added and the mixture refluxed for 4 hours. After cooling to 10° C., 24.4 g. of 4-dimethylaminopyridine and 41.6 g. of 4-(n-hexadecylamino)benzoyl chloride hydrochloride are added. Chloroform and water are added after 16 hours and the chloroform extract is dried and evaporated to dryness. The residue is dissolved in acetic acid and hydrogenated at 30 psi hydrogen pressure over palladium block. After filtration and dilution with water, the 4-hydroxy-3-hydroxymethyl-2-pentyl 4-(n-hexadecylamino)benzoate is obtained as a white solid.

We claim:

1. A compound of the formula:

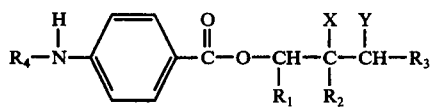

wherein $R_4$ is an unbranched or branched alkyl group, $C_nH_{2n+1}$ wherein $n$ is 8 to 19; $R_1$, $R_2$ and $R_3$ are selected from the group consisting of hydrogen, $C_1$-$C_3$ alkyl, and $C_1$-$C_3$ hydroxyalkylene; X and Y, which may be the same or different, are selected from the group consisting of hydrogen, hydroxy, lower alkanoyloxy, hydroxymethyl, and when taken together X and Y can comprise a carbon-carbon bond; wherein the 4-alkylaminobenzoyloxy moiety and X may be interchanged; with the proviso that when $R_1$, $R_2$ and $R_3$ are all hydrogen or $C_1$-$C_3$ alkyl, then X and Y may not both be hydrogen; and the pharmaceutically acceptable salts thereof.

2. A compound according to claim 1, wherein $R_4$ is an unbranched or branched alkyl group, $C_nH_{2n+1}$ wherein $n$ is 8 to 19; $R_1$, $R_2$ and $R_3$ are hydrogen; X and Y, which may be the same of different, are selected from the group consisting of hydroxy or lower alkanoyloxy, and, when taken together X and Y can comprise a carbon-carbon bond wherein the 4-alkylaminobenzoyloxy moiety and X may be interchanged; and the pharmaceutically acceptable salts thereof.

3. The compound according to claim 1, 2,3-dihydroxypropyl 4-(n-hexadecylamino)benzoate.

4. The compound according to claim 1, 2,3-dihydroxypropyl 4-(n-hexadecylamino)benzoate hydrochloride.

5. The compound according to claim 1, 2-acetoxy-3-hydroxypropyl 4-(n-hexadecylamino)benzoate.

6. The compound according to claim 1, 1,3-dihydroxy-2-propyl 4-(n-hexadecylamino)benzoate.

7. The compound according to claim 1, 4-hydroxybutyl 4-(n-hexadecylamino)benzoate.

8. The compound according to claim 1, 3-hydroxypropyl 4-(n-hexadecylamino)benzoate.

9. The compound according to claim 1, 2-hydroxypropyl-4-(n-hexadecylamino)benzoate.

* * * * *